United States Patent [19]

Tsao

[11] Patent Number: 5,858,996
[45] Date of Patent: Jan. 12, 1999

[54] COMPOSITIONS AND METHODS FOR STABILIZING POLYMERS

[75] Inventor: Fu-Pao Tsao, Lawrenceville, Ga.

[73] Assignee: CIBA Vision Corporation, Duluth, Ga.

[21] Appl. No.: 863,855

[22] Filed: May 27, 1997

Related U.S. Application Data

[63] Continuation of Ser. No. 493,761, Jun. 22, 1995, Pat. No. 5,683,993.

[51] Int. Cl.$^6$ ..................................................... A01N 57/00
[52] U.S. Cl. ................... 514/108; 424/70.16; 514/114; 514/141; 514/912; 514/913; 514/915; 524/54; 524/124; 524/130; 524/702; 524/710; 524/832
[58] Field of Search ........................ 514/108, 114, 514/141, 912, 913, 915; 524/54, 124, 130, 707, 710, 832; 424/70.16

[56] References Cited

U.S. PATENT DOCUMENTS

| | | | |
|---|---|---|---|
| 3,979,349 | 9/1976 | Fink et al. | 260/29.6 |
| 4,290,930 | 9/1981 | Nolken | 260/29.6 |
| 4,303,568 | 12/1981 | May | 260/29.6 |
| 4,474,916 | 10/1984 | Streit | 524/130 |
| 4,540,738 | 9/1985 | Zimmermann | 524/707 |
| 4,607,038 | 8/1986 | Ogata et al. | 514/291 |
| 4,615,697 | 10/1986 | Robinson | 604/890 |
| 4,812,173 | 3/1989 | Tsao et al. | 134/27 |
| 4,889,689 | 12/1989 | Tsao | 422/30 |
| 4,892,679 | 1/1990 | Blum et al. | 514/108 |
| 4,900,469 | 2/1990 | Furr et al. | 252/96 |
| 4,960,799 | 10/1990 | Nagy | 514/567 |
| 5,075,104 | 12/1991 | Gressel et al. | 424/78.04 |
| 5,091,451 | 2/1992 | Kahle et al. | 524/124 |
| 5,192,535 | 3/1993 | Davis et al. | 424/78.04 |
| 5,340,572 | 8/1994 | Patel et al. | 424/78.04 |
| 5,380,303 | 1/1995 | Holly | 604/290 |
| 5,397,567 | 3/1995 | Loebering et al. | 424/78.04 |
| 5,458,873 | 10/1995 | Kawashima et al. | 424/78.04 |
| 5,500,186 | 3/1996 | Mowrey-McKee et al. | 422/28 |
| 5,603,929 | 2/1997 | Desai et al. | 514/914 |

FOREIGN PATENT DOCUMENTS

| | | |
|---|---|---|
| 0354186 | 7/1989 | European Pat. Off. . |
| 0544377A1 | 11/1992 | European Pat. Off. . |
| 0638685A1 | 8/1994 | European Pat. Off. . |
| 2743764 | 9/1977 | Germany . |
| 586251 | 4/1993 | Japan . |
| WO9412723 | 6/1994 | WIPO . |

OTHER PUBLICATIONS

Noveon AA1 (Polycarbophil) Bibliography, Noveon High Performance Pplymers for Pharmaceuticals, The BF Goodrich Company.
Patent Bibliography, pp. 29–32, 25–27.
"Carbopol Troubleshooting Guide", BF Goodrich Specialty Polymers & Chemical Divison, Feb. 1988.
Dequest 2060 Organophosphorus Product, Monsanto, pp. 1–25, Tech Bulletin No. IC/SCS–322.

*Primary Examiner*—Veronica P. Hoke
*Attorney, Agent, or Firm*—R. Scott Meece; Michael U. Lee

[57] ABSTRACT

Compositions and methods for reducing the decomposition rate of polymeric bioadhesives and viscosity enhancers, such as poly(acrylic acids). The compositions include at least one strong, stable chelating agent, preferably an organophosphorous compound such as diethylene triamine penta (methylene phosphonic acid). These biocompatible compositions are especially useful in the ophthalmic field.

21 Claims, No Drawings

COMPOSITIONS AND METHODS FOR STABILIZING POLYMERS

This is a continuation of Ser. No. 08/493,761 filed Jun. 22, 1995 now U.S. Pat. No. 5,683,993.

BACKGROUND OF THE INVENTION

1. Field of the Invention

This invention relates broadly to compositions and method for stabilizing polymers. In a preferred embodiment, the invention relates to stabilization of bioadhesives and viscosity enhancers in ophthalmic compositions.

2. Description of the Related Art

Water soluble and water swellable (i.e., hydrophilic but water insoluble) polymeric materials are known to be useful as bioadhesives and viscosity enhancers. For example, poly (acrylic acids) are used in ophthalmic solutions or mixtures to increase viscosity, thereby increasing the retention time in the eye. An example of a commercially available viscosity enhancer is NOVEON™ AA-1 resins (polycarbophil) available from B. F. Goodrich.

Typically, polymeric viscosity enhancers and bioadhesives decompose, or are otherwise altered, during extended storage periods. The decomposition of a viscosity enhancer reduces the viscosity of the composition, eventually to a point at which the composition is no longer deemed sufficiently effective. Thus, there exists shelf-life problems with compositions, most notably ophthalmic compositions, which include bioadhesives and viscosity enhancers. Accordingly, there is a need to reduce the rate of decomposition of bioadhesives and viscosity enhancers, and to increase the shelf life of compositions including these polymeric materials.

SUMMARY OF THE INVENTION

An object of the invention is to provide a means for stabilizing polymeric compositions.

Another object of the invention is to provide a means for reducing the decomposition rate of polymeric bioadhesives and viscosity enhancers.

A further object of the invention is to provide a means for increasing shelf life of ophthalmic compositions which include polymeric components.

One embodiment of the invention is a stabilized composition, which includes at least one polymer selected from the group consisting of bioadhesives and viscosity enhancers, and at least one strong chelating agent (e.g., a phosphonic acid-containing chelating agent) capable of complexing with trace amounts of free catalytic metal ions. The chelating agent is believed to complex with trace amounts of metal ions, thereby reducing the free metal ion concentration. This reduction in free metal ion concentration reduces the decomposition rate of the polymer. The compositions, which are especially useful in the ophthalmic field, exhibit increased shelf life.

Another embodiment of the invention is a method of stabilizing a polymeric composition. The method involves providing an ophthalmically compatible composition including a polymer selected from the group consisting of bioadhesives and viscosity enhancers, adding a strong (e.g., a phosphonic acid-containing) chelating agent to the composition, and allowing the chelating agent to complex with free catalytic metal ions in the composition. The composition exhibits a polymer decomposition rate which is less than the decomposition rate of a composition which does not include a strong chelating agent. Thus, the resultant polymeric composition has an improved shelf life.

Yet a further embodiment of the present invention is a polymeric composition having a free metal ion concentration less than an amount which will cause substantial polymeric decomposition over a one year storage period at room temperature.

DESCRIPTION OF THE PREFERRED EMBODIMENTS

The compositions of the present invention include a polymeric material, which acts generally as a bioadhesive or a viscosity enhancer, and a stabilizer. The compositions may contain a wide variety of other components, including active agents, excipients, compatibilizers, aesthetic colorants, and the like. A preferred group of compositions are those which are ophthalmically acceptable, i.e., those which do not produce substantial irritation or damage when contacted with the eye, ocular tissue, or surrounding fluids. The preferred ophthalmic compositions are those which are aqueous.

The innovative compositions and methods of the present invention offer improvements in product quality and stability over extended storage periods. Trace amounts of metal ions (e.g., Fe, Cu, Ca, Mg, transition metals), in solutions or slurries, are believed to catalytically increase In the decomposition rate of bioadhesive and viscosity enhancing polymers. Metal ions which catalytically decompose bioadhesive and viscosity enhancing polymers are termed "catalytic metal ions" herein. The strong, stable chelating agents of the present invention are believed to complex with the surrounding metal ions, thereby reducing the free metal ions available to degrade the polymer. Thus, the strong, stable chelating agents reduce the rate of degradation, decomposition, or other inactivation of the polymer which results in the viscosity of the composition decreasing over time. As a result, the shelf life of the composition and the viscosity quality after any given extended storage period is improved by the present compositions and methods.

Two theories are offered to explain the improved stability and shelf life of the present compositions to improve the reader's understanding of the invention. However, the invention is not limited by the theoretical explanation of the means by which the invention functions. First, it is believed that the use of chelating agents having an ability to complex with free ions better than EDTA offers improvements in composition stability and shelf life. Increases in strength of the attraction of the chelating agent to metal ions reduces the probability the complex will dissociate to give increased free metal ion concentrations. Second, it is believed that the use of chelating agents which are more chemically stable than EDTA offers improvements in composition stability and shelf life. If the complex degrades, e.g. by oxidation, the metal ion will be released from the complex and will return to solution, where it will increase the polymer degradation rate. Thus, the preferred chelating agents of the present invention have a metal ion complexing strength greater than EDTA and are more stable than EDTA.

Preferred stabilizers of the present invention are a group of chelating agents having phosphonic acid or phosphonate groups. A preferred group of chelating agents are organophosphonates, particularly amino tri(lower alkylene phosphonic acids). A variety of such chelating agents are commercially available from Monsanto Company, St. Louis, Mo., and are sold under the trademark DEQUEST®. Examples of such compounds include, without limitation, diethylene triamine penta(methylene phosphonic acid); hexamethylene-diaminetetra (methylenephosphonic acid); ethylenediaminetetra (methylenephosphonic acid); and aminotrimethylene phosphonates. A particularly preferred chelating agent is diethylene triamine penta(methylene phosphonic acid), sold under the trademark DEQUEST® 2060.

The bioadhesive or viscosity enhancing polymers of the present invention may be chosen from a wide range of polymers which are susceptible to viscosity reduction (i.e., by degradation or decomposition catalyzed by free metal ions) over time periods of about 30 days to about a year. A preferred group of polymers are those which are cross-linked and have carboxy- and/or hydroxy-functional groups. These bioadhesives or viscosity enhancers include, without limitation thereto. poly(acrylic acids), acrylate copolymers, crosslinked polyacrylic acids, and the like and mixtures thereof Examples of such a polymeric materials which are commercially available are NOVEON™ (polycarbophil) resins (B. F. Goodrich, Cleveland, Ohio), which are water insoluble poly(acrylic acids). Other examples are CARBOPOL® resins (B. F. Goodrich) which are water soluble poly(acrylic acids).

In one embodiment, the present compositions are ophthalmic compositions which include a tonicity agent. The tonicity agent is preferably an alkali metal salts, especially sodium chloride. The tonicity agent is present in an amount which is sufficient to achieve an ophthalmically compatible composition. The tonicity agent may be present in an amount from about 0 to 1.2 weight percent, more preferably about 0.6 to 1.2 weight percent, and most preferably about 0.9 weight percent.

The ophthalmic composition may include an ophthalmic delivery agent. The ophthalmic delivery agents useful in accordance with the present invention may be selected from a wide variety of ophthalmically acceptable agents, including beneficial pharmaceutical agents, diagnostic agents, vitamins, nutrients, lubricants, and the like. The ophthalmic delivery agent may include, without limitation thereto, 3H-thymidine, acetylcholine chloride, acyclovir, adrenaline, amethocaine, aminocaproic acid, antazoline phosphate, arachidonic acid, atropine, benoxinate hydrochloride, betaxolol hydrochloride, bupivacaine, carbachol, carteolol, chloramphenicol, chlortetracycline hydrochloride, chymatrypsin, clonidine, cocaine, corynanthine, cromolyn sodium, cyclopentolate, demecarium bromide, dexamethasone, dibutoline, dichlorphenamide, diclofenac, dipivefrin hydrochloride, echodtiophate iodide, ephedrine, epinephrine bitartrate, erythromycin, ethambutol, etidocaine, eucatropine, fluoromethalone, fluorometholone, gentamicin sulfate, gramicidine, H-thymidine, homatropine hydrobromide, hyaluronic acid, hydrocortisone, idoxuridine, indomethacin, inositol triphosphate, inositol phosphates, isoflurophate, isosorbide, lachesine, levobunolol, levocabastine, lidocaine, lignocaine, medrysone, mepivacaine, methacholine, methazolamide, naphazoline hydrochloride, natamycin, neomycin sulfate, neostigmine, noradrenaline, ofloxacin, oxybuprocaine, oxymetazolin, oxyphenonium, pheniramine maleate, phenylephrine hydrochloride, phosphatidylinositol phosphates, physostigmine, pilocarpine hydrochloride, polyhexamethylene biguanides, polymyxin B sulfates, prednisolone sodium phosphate, proparacaine hydrochloride, proxymethacaine, pyrilamine maleate, scopolamine hydrobromide, sorbinil, sulfacetamide, sulfisoxazole disolamine, tamoxifen, tetracaine hydrochloride, tetracycline tetrahydrozoline hydrochloride, timolol maleate and hemihydrate, trifluridine. tropicamide, vidarabine, and other ophthalmically acceptable salts thereof and mixtures thereof.

While the ideal concentration of the ophthalmic delivery agent will depend on a number of factors, the concentration will generally fall within 0.001 and 10 weight percent. Preferably, the ophthalmic delivery agent is present in an amount from about 0.01 to 2.0 weight percent. More preferably, the concentration of ophthalmic delivery agent is about 0.1 to 1.5 weight percent.

The ophthalmic composition may include a demulcent, such as, for example, a glucose biopolymer. A preferred glucose biopolymer is dextran. Preferably, the glucose biopolymer is present in an amount from about 0.05 to 5.0 weight percent.

The ophthalmic composition may include other demulcents, such as, for example, a polyalkylene glycol. The polyalkylene glycol is preferably a polyethylene glycol, a polypropylene glycol, or a mixture thereof. Preferably, the polyalkylene glycol is present in an amount from about 0.1 to 2.0 weight percent.

Thus, in a particularly preferred embodiment, the ophthalmic composition includes:

(a) about 0.01 to 2.0 weight percent of a bioadhesive or viscosity enhancing polymer;

(b) about 0.0001 to 0.1 weight percent of a chelating agent having at least one phosphonic acid group;

(c) about 0.1 to 2.0 weight percent poly(alkylene glycol);

(d) about 0 to 0.9 weight percent of a tonicity enhancer;

(e) about 0.01 to 5.0 weight percent of a glucose biopolymer;

(f) about 0.001 to 10 weight percent of a delivery agent; and (g) water.

The present method of stabilizing a polymeric compositions, generally includes providing an ophthalmically compatible composition including a bioadhesive or viscosity enhancing polymer; adding at least one strong, stable chelating agent, preferably including at least one phosphonic acid group, to the composition; and allowing the chelating agent to complex with the free metal ions present in the composition, which free metal ions may degrade the polymer, i.e., "catalytic metal ions". This method is believed to allow for the formation of a metal ion complex and polymer formulation which has a decomposition rate which is less than the decomposition rate of the polymer containing trace amounts of free catalytic metal ions.

The order of mixing the components is not believed to be critical. Thus, each of the components of the ophthalmic composition may be, separately and serially, added to a vessel containing water, or all the components may be added simultaneously. Preferably, the components are added separately, with dispersion or dissolution of each separate component being achieved prior to addition of the next component. However, the present stabilization method is not limited by the order of addition or contact of the components.

The previous disclosure will enable one having ordinary skill in the art to practice the invention. In order to better enable the reader to understand specific embodiments and the advantages thereof, reference to the following examples is suggested.

EXAMPLE I

A composition is prepared by mixing NOVEON AA1 (B F Goodrich), sodium chloride, PEG 400 (a 400 molecular weight polyethylene glycol, available from Fisher Scientific), and Dextran 70 (Spectrum Chem. Mfg. Corp., New Brunswick, N.J.) in water in amounts sufficient to produce the following weight percentages:

0.625% NOVEON AA1
0.6% NaCl
0.2% PEG 400
0.1% dextran
Q.S. with water

The pH is adjusted to 6.8 by adding diluted sodium hydroxide solution. The viscosity of the composition is measured initially and after exposure to a temperature of about 45 ↓ C for about 13 months. An elevated temperature is used in order to accelerate the stability testing. The results are presented in Table 1

COMPARATIVE EXAMPLE II

A second mixture is prepared by mixing components and adjusting pH as in Example I, with the addition of disodium EDTA (ethylene diamine tetraacetate). The second mixture has the following composition:

0.625% NOVEON AA1
0.6% NaCl
0.2% PEG 400
0.1% Dextran 70
0.025% disodium EDTA
Q.S. with water The composition is adjusted to a pH of about 6.8. The viscosity of the composition is measured initially and after exposure to a temperature of about 45 ↓ C for about 13 months. The results are presented in Table 1.

COMPARATIVE EXAMPLE III

A third mixture is prepared by mixing components and adjusting pH as in Example I, with the addition of DEQUEST 2060 (solids content 50%, Monsanto Company, St. Louis, Mo.). The third mixture has the following composition:

0.625% NOVEON AA1
0.6% NaCl
0.2% PEG 400
0.006% DEQUEST 2060
0.1% Dextran 70
Q.S. with water The composition is adjusted to a pH of about 6.8. The viscosity of the composition is measured initially and after exposure to a temperature of about 45 ↓ C for about 13 months. The results are presented in Table 1.

TABLE 1

| Example | Stabilizer | Initial Viscosity (cps) | Viscosity (cps) after 13 mos. at 45 ↓ C |
|---|---|---|---|
| I | none | 932.5 | 250.4 |
| II | 0.025% disodium EDTA | 924.8 | 235.0 |
| III | 0.006% DEQUEST 2060 | 853.3 | 955.5 |

EXAMPLE IV

A fourth mixture is prepared by mixing components and adjusting pH as in Example I. The fourth mixture has the following aqueous composition, which is substantially the same as the composition of Example I, except that the amount of NOVEON differs slightly:

0.570% NOVEON AA1
0.6% NaCl
0.2% PEG 400
0.1% Dextran 70
Q.S. with water

The composition is adjusted to a pH of about 7. The viscosity of the composition is measured initially and after exposure to a temperature of about 100 ↓ C for about 7 days. The results are presented in Table 2.

COMPARATIVE EXAMPLE V

A fifth mixture is prepared by mixing components and adjusting pH as in Example I, with the addition of DEQUEST 2060. The fifth mixture has the following aqueous composition:

0.570% NOVEON AA1
0.6% NaCl
0.2% PEG 400
0.1% Dextran 70
0.006% DEQUEST 2060
Q.S. with water The composition is adjusted to a pH of about 7. The viscosity of the composition is measured initially and after exposure to a temperature of about 100 ↓ C for about 7 days. The results are presented in Table 2.

TABLE 2

| Example | Stabilizer | Initial Viscosity (cps) | Viscosity (cps) after 7 days at 100 ↓ C |
|---|---|---|---|
| IV | none | 362.8 | 30.7 |
| V | 0.006% DEQUEST 2060 | 388.3 | 373.0 |

DISCUSSION OF RESULTS

Examples I and IV show that the viscosity of poly(acrylic acid) mixtures decreases substantially over time. Example II shows that disodium EDTA does not have a significant impact on the polymer stability.

However, surprisingly, Examples III and V show that poly(acrylic acid) mixtures stabilized with a stabilizer containing phosphonic acid groups does not exhibit significantly reduced viscosity during accelerated test procedures. Further, the DEQUEST 2060 stabilizer concentration was less than about 12% of the disodium EDTA stabilizer concentration.

The invention has been described in detail, with reference to certain preferred embodiments, in order to enable the reader to practice the invention without undue experimentation. However, a person having ordinary skill in the art will readily recognize that many of the components and parameters may be varied or modified to a certain extent without departing from the scope and spirit of the invention. Furthermore, titles, headings, or the like are provided to enhance the reader's comprehension of this document, and should not be read as limiting the scope of the present invention. Accordingly, the intellectual property rights to this invention are defined only by the following claims and reasonable extensions thereof.

That which is claimed is:

1. A stabilized composition, comprising:
   (a) about 0.1 to 2.0 weight percent of at least one polymer selected from the group consisting of poly(acrylic acids), acrylate copolymers, crosslinked polyacrylic acids and mixtures thereof; and (b) at least one strong and stable amino tri(lower alkylene phosphonic acid) chelating agent in an amount of about 0.0001 to 0.1 weight percent; and (c) water.

2. A composition of claim 1, wherein said composition is ophthalmically compatible.

3. A composition of claim 2, further including an ophthalmic delivery agent.

4. A composition of claim 3, wherein said ophthalmic delivery agent is selected from the group consisting of ophthalmically beneficial pharmaceutical agents, diagnostic agents, vitamins, nutrients, lubricants, and mixtures thereof.

5. A composition of claim 4, wherein said ophthalmic delivery agent is selected from the group consisting of 3H-thymidine, acetylcholine chloride, acyclovir, adrenaline, amethocaine, aminocaproic acid, antazoline phosphate, arachidonic acid, atropine, benoxinate hydrochloride, betaxolol hydrochloride, bupivacaine, carbachol, carteolol, chloramphenicol, chlortetracycline hydrochloride, chymatrypsin, clonidine, cocaine, corynanthine, cromolyn sodium, cyclopentolate, demecarium bromide, dexamethasone, dibutoline, dichlorphenamide, diclofenac, dipivefrin hydrochloride, echodtiophate iodide, ephedrine, epinephrine bitartrate, erythromycin, ethambutol, etidocaine, eucatropine, fluoromethalone, fluorometholone, gentamicin sulfate, gramicidine, H-thymidine, homatropine hydrobromide, hyaluronic acid, hydrocortisone, idoxuridine, indomethacin, inositol triphosphate, inositol phosphates, isoflurophate, isosorbide, lachesine, levobunolol, levocabastine, lidocaine, lignocaine, medrysone, mepivacaine, methacholine, methazolamide, naphazoline hydrochloride, natamycin, neomycin sulfate, neostigmine, noradrenaline, ofloxacin, oxybuprocaine, oxymetazolin, oxyphenonium, pheniramine maleate, phenylephrine hydrochloride, phosphatidylinositol phosphates, physostigmine, pilocarpine hydrochloride, polyhexamethylene biguanides, polymyxin B sulfates, prednisolone sodium phosphate, proparacaine hydrochloride, proxymethacaine, pyrilamine maleate, scopolamine hydrobromide, sorbinil, sulfacetamide, sulfisoxazole disolamine, tamoxifen, tetracaine hydrochloride, tetracycline, tetrahydrozoline hydrochloride, timolol maleate and hemihydrate, trifluridine, tropicamide, vidarabine, other ophthalmically acceptable salts thereof and mixtures thereof.

6. A composition of claim 1, wherein said polymer is a poly(acrylic acid). phosphonic acid).

7. A composition of claim 1, wherein said chelating agent is selected from the group consisting of diethylene triamine penta(methylene phosphonic acid); hexamethylenediaminetetra (methylenephosphonic acid); ethylenediaminetetra (methylenephosphonic acid); aminotrimethylene phosphonates; and mixtures thereof.

8. A composition of claim 7, wherein said chelating agent is diethylene triamine penta(methylene phosphonic acid).

9. A composition of claim 1, further comprising about 0.1 to 2.0 weight percent poly(alkylene glycol).

10. A composition of claim 1, further comprising about 0.6 to 1.2 weight percent of a tonicity enhancer.

11. A composition of claim 10, wherein said tonicity enhancer is sodium chloride.

12. A composition of claim 1, further comprising about 0.05 to 5.0 weight percent of a glucose biopolymer.

13. A composition of claim 12, wherein said glucose biopolymer is dextran.

14. A composition of claim 1, comprising:

(a) about 0.01 to 2.0 weight percent of said polymer;

(b) about 0.0001 to 0.1 weight percent of said chelating agent;

(c) about 0.1 to 2.0 weight percent poly(alkylene glycol);

(d) about 0 to 1.2 weight percent of a tonicity enhancer;

(e) about 0.05 to 5.0 weight percent of a glucose biopolymer;

(f) about 0.001 to 10 weight percent of a delivery agent; and (g) water.

15. A composition of claim 14, comprising:

(a) about 0.01 to 2.0 weight percent of a polymer selected from the group consisting of poly(acrylic acids), acrylate copolymers, crosslinked polyacrylic acids, and mixtures thereof;

(b) about 0.0001 to 0.1 weight percent of an organophosphorus chelating agent;

(c) about 0.1 to 2.0 weight percent poly(alkylene glycol) selected from the group consisting of polyethylene glycol, polypropylene glycol, and mixtures thereof;

(d) about 0 to 1.2 weight percent of an ophthalmically compatible alkali halide tonicity enhancer;

(e) about 0.05 to 5.0 weight percent of a glucose biopolymer;

(f) about 0.001 to 10.0 weight percent of a delivery agent; and (g) water.

16. A method of stabilizing a polymer composition, comprising the steps of:

(a) providing an ophthalmically compatible composition including about 0.1 to 2.0 weight percent of a polymer selected from the group consisting of poly(acrylic acids), acrylate copolymers, crosslinked polyacrylic acids and mixtures thereof;

(b) adding at least one strong and stable amino tri(lower alkylene phosphonic acid) chelating agent in an amount of about 0.0001 to 0.1 weight percent and water; and (c) allowing said chelating agent to complex with free catalytic metal ions, thereby producing a composition with metal ion complexes, whereby the polymer in said composition has a decomposition rate which is less than the decomposition rate of the uncomplexed composition.

17. A method of claim 16, further including an ophthalmic delivery agent selected from the group consisting of ophthalmic beneficial pharmaceutical agents, diagnostic agents, vitamins, nutrients, lubricants, and mixtures thereof.

18. A method of claim 16, wherein said chelating agent is selected from the group consisting of diethylene triamine penta(methylene phosphonic acid); hexamethylenediaminetetra (methylenephosphonic acid); ethylenediaminetetra (methylenephosphonic acid); aminotrimethylene phosphonates; and mixtures thereof.

19. A method of claim 18, wherein said chelating agent is diethylene triamine penta(methylene phosphonic acid).

20. A method of claim 16, wherein said polymer composition comprises:

(a) about 0.01 to 2.0 weight percent of said polymer;

(b) about 0.0001 to 0.1 weight percent of said chelating agent;

(c) about 0.1 to 2.0 weight percent poly(alkylene glycol);

(d) about 0 to 1.2 weight percent of a tonicity enhancer;

(e) about 0.05 to 5.0 weight percent of a glucose biopolymer;

(f) about 0.001 to 10 weight percent of a delivery agent; and (g) water.

21. A method of claim 20, wherein said polymer composition comprises:

(a) about 0.01 to 2.0 weight percent of a polymer selected from the group consisting of poly(acrylic acids), acrylate copolymers, crosslinked polyacrylic acids, and mixtures thereof;

(b) about 0.0001 to 0.1 weight percent of an organophosphorus chelating agent;

(c) about 0.1 to 2.0 weight percent poly(alkylene glycol) selected from the group consisting of polyethylene glycol, polypropylene glycol, and mixtures thereof;

(d) about 0 to 1.2 weight percent of an ophthalmically compatible alkali halide tonicity enhancer;

(e) about 0.05 to 5.0 weight percent of a glucose biopolymer;

(f) about 0.001 to 10 weight percent of a delivery agent; and (g) water.

* * * * *